United States Patent [19]

Dreyfus et al.

[11] 4,283,147
[45] Aug. 11, 1981

[54] ELECTRO-OPTICAL SCANNING SYSTEM

[75] Inventors: Marc G. Dreyfus, Old Greenwich; Arnold Pellman, Stamford, both of Conn.

[73] Assignee: Dreyfus-Pellman, Stamford, Conn.

[21] Appl. No.: 48,632

[22] Filed: Jun. 14, 1979

[51] Int. Cl.³ .............................................. G01N 21/55
[52] U.S. Cl. ..................................... 356/445; 350/449
[58] Field of Search ................. 356/429–431, 237, 445, 356/447, 448; 350/175 TS, 91, 45, 206

[56] References Cited

U.S. PATENT DOCUMENTS 3,909,602  9/1975  Micka .............................. 356/237 X Primary Examiner—John K. Corbin
Assistant Examiner—Bruce Y. Arnold
Attorney, Agent, or Firm—Michael Ebert

[57] ABSTRACT

A defocusable electro-optical system for scanning the near-specular surface of an object to be examined with a light beam to produce a reflected-light pattern that depends on the relative reflectivity of the different components which make up the surface. The system includes a light source producing an illumination beam that is directed by a scanning mechanism through an objective which focuses the beam onto the surface to be examined. The beam reflected from the surface is directed toward a photodetector through a field stop that defines the size of the viewed area when the object surface lies in the focal plane. The viewed object surface is illuminated in a manner imaging thereon an image of the light source comparable in size to the field stop, so that when the object surface lies in the focal plane the light source image is coincident therewith. When the object surface is axially displaced from the focal plane and is out of focus, the light source image assumes an aerial position between the objective and the object surface and is relayed by the objective to function as a virtual stop whose aperture deletes that portion of the rays reflected from the object surface which otherwise cause the image of the object to blur, thereby eliminating defocus-blurring of the object image.

7 Claims, 5 Drawing Figures

U.S. Patent  Aug. 11, 1981  4,283,147
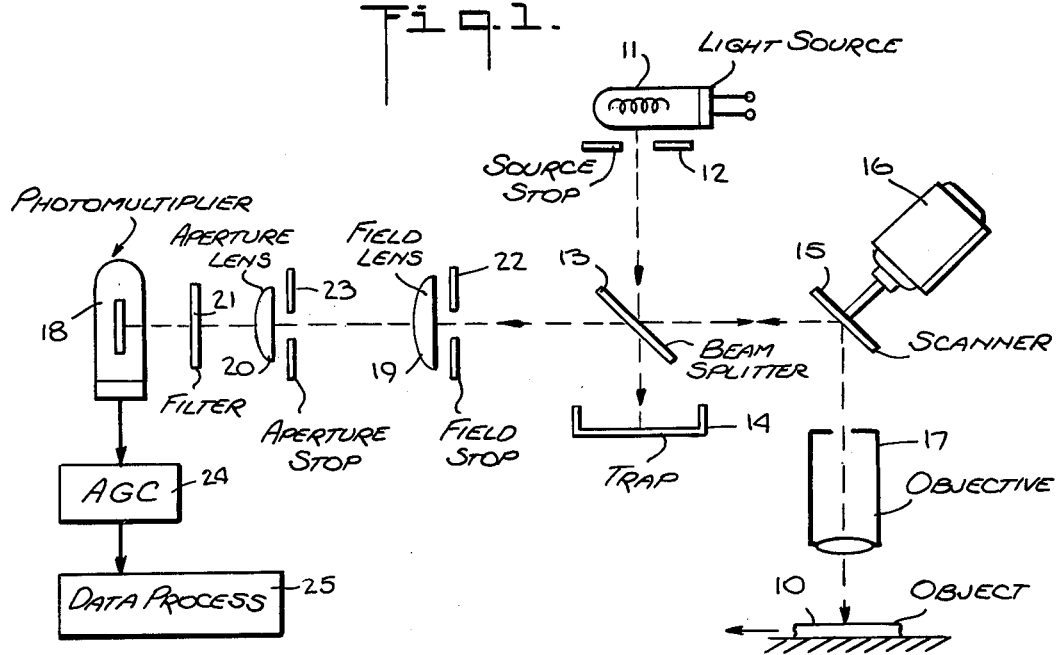
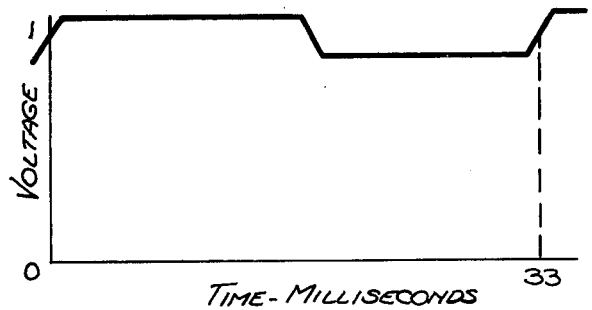
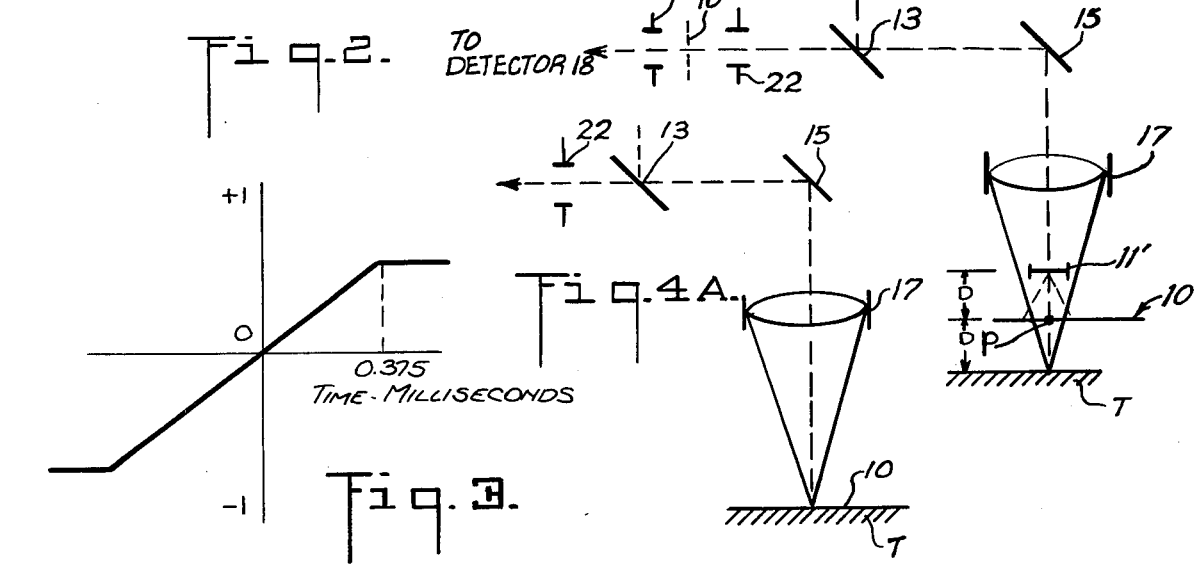

ELECTRO-OPTICAL SCANNING SYSTEM

BACKGROUND OF INVENTION

1. Field of Invention:

This invention relates generally to non-contact electro-optical scanning systems for the inspection and measurement of opaque objects having a quasi-specular surface which, when illuminated exhibits a light reflection pattern that depends on its physical structure, and more particularly to a defocusable static system of this type which functions to prevent image blurring when the object being examined is out of focus.

2. Description of the Prior Art:

Electro-optical scanning systems are known that are capable of scanning an opaque object with a light beam to produce a reflected beam which is detected to generate a video signal whose waveform represents the field of view. The present invention is applicable to the electro-optical inspection and measurement of an opaque object having a relatively smooth surface which is quasi-specular and exhibits a reflection pattern that is indicative of its physical formation.

Thus, integrated circuits are constituted by smooth substrates whose reflectivity differs from that of conductive paths and circuit elements formed thereon. The present invention is capable of illuminating the surfaces of such objects with a scanning beam to inspect the formation thereof. However, in the interest of simplicity, we shall consider by way of example an opaque object constituted by a bronze sheet of spring material having a gold inlay therein, this material being usable in making electrical connectors for telephone systems.

We shall first assume that the object being scanned is made entirely of bronze sheeting. Then the surface thereof would be uniformly reflective and the output signal of the electro-optical system would have a flat and featureless waveform, the even level of the resultant signal representing the uniformly reflective surface intercepted by the scanning beam. When, however, the object has a bronze surface interrupted by a gold inlay whose reflectivity differs from that of bronze, then the scanning system will function as an edge tracker to determine the position of the inlay by measuring the change in reflection that occurs at the edge thereof. In this instance, the waveform of the output signal will exhibit a voltage step indicative of the presence of a gold inlay in an otherwise constant signal level.

The conventional electro-optical scanning system generates in its focal plane an image of the object being scanned, this plane being perpendicular to the optical axis of the system and passing through the focus thereof. The image generated attains its maximum resolution or sharpness when the object being examined is at a predetermined distance from the lens with respect to which it is then "in focus." As the object is displaced in either axial direction from this focal distance, its image becomes blurred and therefore loses resolution.

Such image blurring or defocusing has heretofore been accepted as an inevitable concomitant of any optical scanning system of the static type. By a static optical system is meant one whose lenses have fixed positions and are therefore not axially movable to refocus the system with respect to an object being viewed which is subject to displacement relative to the focal plane.

Thus when the object to be examined is formed of a continuous strip of spring metal that is being advanced in the course of production, it is as a practical matter impossible to maintain the position of this longitudinally-moving strip exactly in the focal plane of the optical system, for the strip tends to move up and down relative to the track on which it is supported. Since the vertical displacement of the strip with respect to the focal plane is random and intermittent, one cannot use a dynamic optical system whose focus is adjustable. There is no practical way, in a high speed scanning system, by which the adjustment of focus can automatically be correlated with the changing position of the object being examined.

A similar depth-of-focus problem exists in the microcircuit industry, where microcircuit printing masks are aligned relative to the finely detailed imagery on a partially completed wafer. In this application, alignment accuracy of better than 10 microinches is required between mask and wafer. However, the mask and wafer must be kept apart, separated by an air gap of several milliinches during the alignment process in order to avoid abrading and damaging their surfaces. This separation imposes a severe depth-of-focus requirement on the alignment process which is difficult to meet with conventional technology.

The prevailing assumption that defocusing is unavoidable in a conventional static optical scanning system wherein the object position is unstable is based on the fact that a system of this type has a single field stop that defines the instantaneous field of view, the field stop having a fixed position within the optical system. Sharp images of this field stop are generated by the static optical system in defined and fixed conjugate planes. Any deviation of the viewed object surface from such a conventional conjugate focal plane unavoidably gives rise to defocus and blurring of the image, with a consequent loss in measurement accuracy.

While it is possible to compensate for image blurring by processing the waveform of the output signal of the electro-optical system, this processing must take into account the comparative brightness of neighboring points in the image. To do so entails complex and costly image data processing apparatus.

SUMMARY OF INVENTION

In view of the foregoing, the main object of this invention is to provide a defocusable, non-contact, electro-optical scanning system of the static type for inspecting and measuring the quasi-specular surface of an opaque object, which system effectively enlarges the depth of focus and thereby reduces defocus-blurring when the object is displaced from the focal plane.

More particularly, an object of this invention is to provide a defocusable electro-optical scanning system that prevents blurring by automatically deleting from the system that portion of the light flux which otherwise would have caused the image to blur. Hence while the resultant afocal image becomes dimmer as the object is displaced from the focal plane, it remains sharp.

A salient advantage of a defocusable, static optical system in accordance with the invention is that it constitutes a powerful tool for automatic image recognition and alignment, for it simplifies, to a meaningful degree, the requisite image data processing. In practice, after the image has been converted into a corresponding electrical waveform, image dimming, as a result of a displacement of the object from the focal plane can readily be compensated for by an automatic gain control operation.

Briefly stated, these objects are attained in a static electro-optical scanning system in accordance with the invention in which a light beam from a light source is directed by a scanning mechanism through an objective which focuses the scanning beam onto the surface of an opaque object to be inspected, the surface being quasi-specular to produce a reflection pattern that depends on the relative reflectivity of the different components which make up the surface.

The scanning beam reflected from the surface is directed toward a photodetector through a field stop defining the size of the viewed area when the object plane is in best focus. The object surface is illuminated by imaging thereon an image of the light source comparable in size to that of the field stop, the illuminated image of the light source being substantially parfocal with this field stop and being scanned in synchronism with it. To provide a source image of the required dimensions, use may be made of a light source whose incandescent filament is of the appropriate size. For other sources, a stop external thereto may be used.

If the viewed object moves toward the objective and is thereby displaced from the focal plane, the light source image (which, when the object surface lies in the focal plane, is coincident therewith) assumes an aerial position between the objective and the object surface and is relayed by the objective to function as a virtual stop whose aperture deletes that portion of the rays reflected from the out-of-focus object which otherwise cause defocus blurring of the object image. As a consequence of this action, the reflected light from the object surface as seen by the photodetector assumes its maximum brightness when the object surface lies in the focal plane and becomes dimmer but without blurring to the degree that the object surface departs from the focal plane, this dimming being compensated for by an automatic gain control.

OUTLINE OF DRAWINGS

For a better understanding of the invention as well as other objects and further features thereof, reference is made to the following detailed description to be read in conjunction with the accompanying drawings, wherein:

FIG. 1 is a schematic diagram of a defocusable electro-optical scanning system in accordance with the invention;

FIG. 2 is a waveform representing the signal output of the photodetector included in the system;

FIG. 3 is a waveform showing the processed signal output; and

FIGS. 4 A and B are schematic diagrams explanatory of the operation of the system.

DESCRIPTION OF INVENTION

The Electro-Optical System

Referring now to FIG. 1, which schematically illustrates a defocusable electro-optical system in accordance with the invention, we shall assume that an object 10 being examined is a moving strip of bronze sheeting having a gold inlay therein. The system is adapted to recognize the low contrast image boundary resulting from the degree of reflectivity of the gold inlay which differs from that of the bronze sheeting. The change in reflection at the edge of the inlay is measured by a spot of light which is swept back and forth across the edge in a scanning motion.

Illumination is provided by a single tungsten light bulb 11 which in one practical embodiment of the invention serves to generate a tiny rectangle of light $0.004'' \times 0.016''$ in size on the quasi-specular surface of the object. Alternatively, to ensure a light beam having the desired cross-sectional dimensions for other light sources, a light source stop 12 combined with a relay lens between source 11 and stop 12 may be provided. Light from source 11 is directed toward a beam splitter 13 whose semi-reflective surface permits a portion of the light energy to pass directly therethrough to be absorbed by a light trap 14, the remaining energy being reflected at right angles to the source beam path toward a scanning mirror 15 driven by a motor 16.

In practice, the scanning mirror surface is tilted approximately two degrees relative to the plane perpendicular to the shaft of motor 16. The light reflected from the scanning mirror 15 is focused onto the surface of object 10 by a microscope objective 17. The light reflected from the surface of object 10 is directed in the reverse direction through objective 17, scanning mirror 15 and beam splitter 13 toward a photomultiplier 18 or other suitable photodetector.

The light detection system further includes a field lens 19, an aperture lens 20 and a spectral filter 21, the filter optimizing edge contrast. The field of view of the detection system is defined by a field stop 22 which is made parfocal (i.e., having corresponding focal points all in the same plane) and coaxial with the light source by beam splitter 13 so that the detection system is sensitive only to rays from the object surface which is brightly illuminated by the light source. In this manner, the detection system is locked into the illuminated spot and both are scanning synchronously around the optical axis.

The detection system is further constrained by an aperture stop 23 so that it receives light only from a limited area at the plane of the exit pupil of the microscope objective 17. This additional constraint has the advantage of reducing the effect of stray light on the system. Aperture stop 23 can also be used to vignette the light transmitted to the photomultiplier 18 in a cyclical manner in order to compensate for extraneous modulated signals generated by the scanning system.

Optical scanning systems tend, in general, to generate faint false signals which masquerade as low contrast imagery in the field of view. These false signals limit the accuracy of the system, and its ability to measure real images with low contrast. For example, beam splitter 13 may be an uncoated pellicle oriented at a 45 degree angle to the scanner system's optical axis. As the scanner mirror 15 rotates, the mean incidence angle of the light reflected by the pellicle and detected by the photomultiplier 18 varies a few degrees about 45 degrees. This variation in incidence angle causes a variation in the Fresnel reflectance of the dielectric surfaces of the pellicle, which results in a cyclical false signal in the photomultiplier output when scanning a featureless field of view. This false signal can be compensated by offsetting aperture stop 23 relative to the system's optical axis so that it frames the oscillating image of the exit pupil of microscope objective 17, the oscillating image being generated by scanning mirror 15 and field lens 19. Alternatively, the false signal can be compensated by electronically injecting a matching waveform as part of the electronic signal processing.

The tiny $0.004'' \times 0.016''$ rectangle of light derived from the light source and focused on the surface of the inlaid object 10 is scanned across the surface in an elliptical motion which, in practice, may be at a rate of 30 revolutions per second. The light reflected back from this scanning rectangle is automatically processed to determine the position of the low-contrast boundary. As the rectangle moves across the object surface, its long 0.016" axis is maintained substantially parallel to the inlay boundary while its center describes a 0.064"×0.045" ellipse with its 0.045" axis parallel to the inlay boundary; hence the rectangle sweeps out an oval area which is 0.068"×0.061" in size with its 0.061" dimension parallel to the inlay boundary.

Photomultiplier 18 converts the scanning light energy reflected from the object surface into a corresponding electrical signal. After amplification in the photomultiplier dynode chain, the resultant signal waveform is that illustrated in FIG. 2, wherein it will be seen that the waveform exhibits a 10% change in voltage each time the scan crosses the image edge during each scanning revolution. Since the elliptical scanning motion on the surface is at a rate of 30 revolutions per second, the period of the voltage waveform is 1/30th of a second.

The signal from photomultiplier 18 is filtered to remove the DC voltage component due to the average brightness in the field of view. Then the signal is fed through an automatic gain control circuit 24 to a data processor 25 where the signal is amplified in a feedback amplifier and normalized to a constant peak voltage level. A detailed view of a portion of the resulting signal as it appears in the vicinity of an edge crossing is shown in FIG. 3.

This signal is then differentiated in the data processor to detect the rapid changes in voltage level which occur at crossings of the image edge. The differentiated signal is used to generate a start pulse in the signal-processing logic. This start pulse enables a zero-crossing monitor to look for points in the signal waveform at which the signal voltage is zero. At the next zero-crossing after the start pulse, the logic gates a strobed readout of a rotary digital encoder connected to the scanning mirror. This encoder readout of the angular mirror position is stored as a measurement of the precise position of the image edge.

To discriminate against surface scratches, the logic stores this edge measurement for 1 millisecond, while continuing to monitor the signal waveform. If a second start pulse and zero crossing are observed within 1 millisecond, then the encoder readout is attributed to a scratch or mar, and is dumped. If no other image edge is observed within this 1 millisecond interval (corresponding to 0.006" travel by the scanning rectangle across the metal strip surface), then the edge is validated and transmitted to a second number storage register.

This second storage register is used to accumulate and average a prescribed number of edge measurements. The averaged output is displayed on a digital display, and also converted into an analog voltage for use in the feedback control loop of the metal strip manufacturing machinery.

Defocusable Operation:

In an a defocusable system in accordance with the invention, the depth of focus is enlarged when illuminating and observing an image of the quasi-specular surface of the object under examination, the enlarged depth of focus avoiding blurring when the object surface is axially displaced from the focal plane. As noted in "Modern Optical Engineering," Warren J. Smith (1966), McGraw-Hill Book Company, the concept of depth of focus rests on the assumption that in any given optical system, there exists a blur due to defocusing of a small enough size such that it will not adversely affect the system's performance. The depth of focus is the amount by which the image may be shifted longitudinally with respect to some reference plane (i.e., film plane) and introduce no more than an acceptable blur.

The system uses the specular reflectance characteristic of the object surface to generate a virtual optical stop which effectively reduces the numerical aperture (i.e., enlarges the aperture ratio or f/stop) of the viewing optical system, thereby limiting enlargement of the image circle of confusion due to defocus blurring. The virtual stop reacts automatically and practically instantaneously to changes in defocus position of the object plane. No servomechanisms or mechanical positioning devices are entailed since the system acts passively, and its reaction speed is limited principally by the velocity of light. As noted in the same Smith text, "When an optical system is defocused, the image of a point becomes a blurred spot. The size of the blur is determined by the relative aperture of the system and the focus shift. In the present invention, the virtual stop, whose aerial position in front of the object being viewed depends on the extent of defocus, acts as an aperture stop that limits the bundle of rays that the system can accept, thereby limiting defocus blurring.

The virtual stop can be made to act in a circularly symmetrical manner, so that it limits the defocus blurring as if it were a circular iris diaphragm located in the aperture stop of the viewing system which closes down and opens up in a circularly symmetrical manner. More generally, however, the virtual stop can be made to act in a non-circular manner comparable to an iris diaphragm with a rectangular boundary, or with a boundary shaped like a pair of orthogonal intersecting rectangles of unequal size and aspect ratio. When shaped non-circularly, the virtual stop can allow more blurring (and correspondingly greater light-gathering power) in meridional planes for which blurring has a less critical effect on system performance.

The virtural stop can be made to prevent defocus blurring entirely, or to permit a predetermined maximum amount of defocus blurring to occur before it begins to stop down. The amount of blurring permitted before stopping action begins can be chosen separately and independently for each meridional plane.

A defocusable system in accordance with the invention makes possible significantly improved production tooling for that segment of the metal industry which produces gold inlays on bronze sheet spring material for use in making electrical connectors for telephone systems, computers, and various other electrical applications. It also renders feasible a major advance in production tooling for the microcircuit industry in general, and for microcircuit mask alignment in particular. In these applications, the surfaces viewed are often opaque, usually specular, and must often be located in two or more distinct planes, with separations large compared to the required system resolution.

The virtual stop is generated by illuminating the viewed surface by imaging thereon an image of the light source which is comparable in size to the field stop defining the size of the viewed area when the object plane is in best focus. The illuminated light source image is made substantially parfocal with the field stop, and is scanned in synchronism with it by means of a scanning mirror/beam splitter arrangement illustrated in FIG. 4.

FIGS. 4A and 4B schematically illustrate the optical relationships that prevail when the image is in-focus and out of focus, respectively in the system including light source 11 (illustrated only in FIG. 4B), beam splitter 13, scanning mirror 15 and objective 17. In the in-focus condition, the object being examined lies on a track T, the plane of the object being represented by numeral 10. The plane of the illuminated image of the light source 11 constituted by an incandescent filament of specified dimensions, then exactly coincides with object plane 10.

In practice, objective 17 may be a ten-power microscope objective, and the field stop 22 of the system through which passes light optically relayed by objective 17 toward photodetector 18, may be an oblong slot 0.04 inch by 0.16 inch in size.

When, however, object plane 10 is caused to lift above track T, as shown in FIG. 4B, by a distance D and the system is then defocused, the plane of the light source image of light source 11 comes to focus in mid-air at an axial distance 2D from track T to form an aerial light source image 11'. In this defocus condition, an image of object plane 10 and of light source image 11' are optically relayed by objective 17 to respective positions behind stop 22 in the optical path leading to photodetector 18, thereby creating an object plane image 10' and a relayed light source image 11''.

In the defocus condition, the plane of relayed light source image 11'' is separated from the plane of field stop 22 by approximately the square of the magnification ratio between light source image 11' and relayed light source image 11'' times the distance 2D. Both field stop 22 and relayed light source image 11'' then function as active field stops as well as active aperture stops and operate together to determine the area on object plane image 10' which is illuminated by light source 11 and visible through stop 22 so that it can be viewed by detector 18.

In the defocus condition, some of the light flux transmitted by objective 17 from the aerial light source image 11' to the relayed light source image 11'' is blocked by field stop 22 and appears as a light spill around the edges of this stop on the side thereof facing beam splitter 13. The area viewed in the object plane 10 is likewise delimited by the action of the aerial light source image 11' which, in effect, functions as a virtual stop.

Use of the defocusable system is restricted to object surfaces which act as specular or near specular light reflectors, the system not being operable on highly diffuse-reflective or Lambertian surfaces. In this context it is important to characterize the limited degree of specularity required for operation of a defocusable system.

An optical surface is conventionally considered to reflect in a specular manner when images viewed through the surface appear sharp and clear. If the reflected images are viewed with a naked eye, then the reflecting surface may be considered to be specular when it reflects light with ray deviations small compared to the one minute of arc resolution capability of the well-corrected human eye.

In the present invention, the quality of specularity required has been termed "quasi-specular" because it is typically relatively crude. For example, a scanner embodying this invention has been constructed for scanning gold-inlaid bronze spring surfaces with which the virtual stop generated by the light source and the field stop are both 0.004" wide as measured on the metal surface. The metal surface can move out of focus as much as 0.015", thus producing a separation of 0.030" between the two 0.004" wide stops. In this case the degree of directivity of reflection required of the surface is merely that it reflect near-specularly to better than 0.004"/0.030"=0.13 radian or 460 minutes of arc.

In the defocusable system, the source stop can be the incandescent tungsten filament itself or equivalently can be an aperture 12 in an illuminated plane to which light is delivered from a remote light source. An image of the source stop is generated and focused onto the object plane, where it is scanned around by the tilted rotating mirror 15 or an equivalent scanning mechanism.

If the object plane is located in the ideal focal plane, then a sharply defined image of the source stop is generated on the object plane. As this image is scanned around the object plane, its reflected energy is relayed by the same scanner mirror to a matching image stop (field stop 22) located at a focal plane which is conjugate to the in-focus object plane. The scanning mirror generates a stationary image of the scanning spot at the image stop plane. If the image stop is no smaller than the source stop, then it is redundant and inoperative when the system is in focus.

If the object plane is not at the focus position, then a blurred image of the source stop is generated at the image stop plane. The image stop (field stop 22) then interacts with the source stop image to select and transmit to the photodetector only those light rays reflected by the small area on the object which would have been illuminated by the critically focused source image. In effect, the object plane and the two stops interact to select only those light rays emanating from the source stop which intersects the object plane in a sharply defined area equal in size to the average of the stop sizes.

It should be noted that in the defocusable system in accordance with the invention, the object plane need not be a perfectly specular reflector. All that is required of it is the generation of a relatively localized image of the source stop at the small distances from the surface of the object plane which are comparable in magnitude to the defocus motion. Thus it has been demonstrated experimentally with the inlay scanner that object planes with 10 microinch RMS roughness permit effective defocusable operation with a 0.004" wide scanning stop in the presence of as much as 0.040" defocus motion.

While there has been shown a preferred embodiment of a defocusable electro-optical scanning system in accordance with the invention, it will be appreciated that many changes and modifications may be made therein without, however, departing from the essential spirit thereof.

I claim:

1. A defocusable electro-optical system for scanning the quasi-specular surface of an object to be examined with a light beam to produce a reflection light pattern that depends on the relative reflectivity of the different components which make up the surface, said system comprising:
  A. a light source producing an illumination beam;
  B. an objective for focusing light on said object surface;
  C. a scanning mechanism to direct said illumination beam through said objective to focus said beam onto said surface when said surface lies in the focal plane which is perpendicular to the optical axis of the objective, said object being subject to axial displacement relative to said plane;

D. a photodetector;

E. means to direct the beam reflected from said surface through a field stop onto said photodetector which yields a signal depending on the relative reflectivity of said components as the illustrated beam scans across said surface, said field stop limiting the size of the viewed area when the object surface lies in the focal plane; and F. means illuminating the viewed object surface in a manner imaging thereon an image of the light source comparable in size to the field stop whereby, when the object surface lies in the focal plane, the light source image is coincident therewith, and when the object surface is axially displaced from the focal plane and is out of focus, the light source image assumes an aerial position between the objective and the object surface and is relayed by the objective to function as a virtual stop, said virtual stop serving to delete that portion of the rays reflected from the object surface which otherwise would cause the image of the object to blur, thereby to limit defocus-blurring of the object image.

2. A system as set forth in claim 1, wherein said light source is an incandescent bulb whose filament is dimensioned to produce said light source image which constitutes the virtual stop.

3. A system as set forth in claim 1, wherein said virtual stop is created by a stop associated with the light source to restrict the rays therefrom to create said light source image.

4. A system as set forth in claim 1, further including an automatic gain control device in the output of said photodetector to compensate for the reduction in signal volume when the light received from the object dims when the object surface is displaced from the focal plane.

5. A system as set forth in claim 1, further including a beam splitter in the path of said illumination beam said beam splitter positioned to direct said beam at a right angle to the beam from said light source and toward said scanning mechanism, which then directs the beam through said objective and onto the surface of the object so that light that is reflected from the object passes back through the scanning mechanism and is transmitted by said beamsplitter to said photodetector.

6. A system as set forth in claim 5, wherein said scanning mechanism is constituted by an inclined mirror which is motor driven.

7. A system as set forth in claim 5, further including a spectral filter in the optical path leading toward said photodetector.

* * * * *